(12) United States Patent
Wolfe et al.

(10) Patent No.: US 8,193,941 B2
(45) Date of Patent: Jun. 5, 2012

(54) SNORING TREATMENT

(75) Inventors: Andrew Wolfe, Los Gatos, CA (US); Thomas Martin Conte, Atlanta, GA (US)

(73) Assignee: Empire Technology Development LLC, Wilmington, DE (US)

( * ) Notice: Subject to any disclaimer, the term of this patent is extended or adjusted under 35 U.S.C. 154(b) by 297 days.

(21) Appl. No.: 12/436,550

(22) Filed: May 6, 2009

(65) Prior Publication Data

US 2010/0283618 A1   Nov. 11, 2010

(51) Int. Cl.
*G08B 23/00* (2006.01)
*G10K 11/16* (2006.01)

(52) U.S. Cl. ............... 340/575; 340/573.1; 381/71.11; 381/71.14; 381/71.2

(58) Field of Classification Search ............ 340/575, 340/576, 573.1, 539.1, 407.1; 381/71.11, 381/71.2, 71.6, 71.14; 600/26, 534, 544, 600/590; 128/204.18, 204.23
See application file for complete search history.

(56) References Cited

U.S. PATENT DOCUMENTS

| | | | | |
|---|---|---|---|---|
| 5,444,786 A * | 8/1995 | Raviv | .................. | 381/71.14 |
| 5,774,055 A | 6/1998 | Pomerantz | .................. | 340/573.7 |
| 5,853,005 A | 12/1998 | Scanlon | .................. | 600/459 |
| 6,480,733 B1 | 11/2002 | Turcott | .................. | 600/516 |
| 6,544,199 B1 * | 4/2003 | Morris | .................. | 600/590 |
| 6,553,256 B1 | 4/2003 | Jorgenson et al. | .................. | 607/5 |
| 6,997,882 B1 | 2/2006 | Parker et al. | | |
| 7,248,915 B2 * | 7/2007 | Ronnholm | .................. | 600/544 |
| 7,277,749 B2 * | 10/2007 | Gordon et al. | .................. | 607/2 |
| 7,690,253 B2 | 4/2010 | Noda et al. | | |
| RE41,376 E * | 6/2010 | Torch | .................. | 340/575 |
| 7,835,529 B2 * | 11/2010 | Hernandez et al. | .................. | 381/71.2 |
| 7,866,212 B2 * | 1/2011 | Ariav et al. | .................. | 73/596 |
| 2003/0088196 A1 | 5/2003 | Burton | | |
| 2008/0094226 A1 | 4/2008 | O'Shea et al. | .................. | 340/573.1 |
| 2008/0306706 A1 | 12/2008 | Markovic | | |
| 2009/0147965 A1 * | 6/2009 | Kuo | .................. | 381/71.6 |
| 2009/0182913 A1 | 7/2009 | Rosenblatt et al. | .................. | 710/72 |
| 2009/0278820 A1 | 11/2009 | Fourquin et al. | .................. | 345/184 |
| 2010/0052896 A1 | 3/2010 | Goodman | | |

(Continued)

OTHER PUBLICATIONS

"Snoring and Sleep Apnea", Health Wellness Resources, Information & Resources for Sleep Apnea: Chemistry Behind Sleep Apnea and Snoring (2007), http://wayback.archive.org/web/20071001000000*/http://www.healthwellness1.com/sleepapnea/snoring_and_sleep_apnea.php (Visited Jul. 12, 2011. 8:49 pm) Comments: Obtained Feb. 7, 2007 version from www.waybackmachine.org, 2006, pp. 1-3.

(Continued)

*Primary Examiner* — Van T. Trieu
(74) *Attorney, Agent, or Firm* — Dorsey & Whitney LLP

(57) ABSTRACT

Health-sensing and health-action devices and systems are generally described. The health-sensing device may include one or more of a sensor, a filter, and a transmitter. The sensor may be configured to sense one or more factors relating to an indicator of a health related condition or occurrence such as snoring and may include one or more microphone devices, accelerometers, and/or MEMs devices. The filter may be configured to evaluate a signal from the sensor and determine if the indicator has been detected. The transmitter may be arranged for initiating a transmission based on a signal from the filter. The health-action device may be configured for responding to an indicator of a health related condition or occurrence of a user and may include one or more of a receiver, a processor, and a responder. The health-action device may stimulate the user or may cancel the snoring sound.

28 Claims, 9 Drawing Sheets

U.S. PATENT DOCUMENTS

| | | | |
|---|---|---|---|
| 2010/0217158 A1 | 8/2010 | Wolfe et al. | 600/595 |
| 2010/0217345 A1 | 8/2010 | Wolfe et al. | 607/17 |
| 2010/0226491 A1 | 9/2010 | Conte et al. | |
| 2010/0261984 A1 | 10/2010 | Tsai et al. | |
| 2010/0286545 A1 | 11/2010 | Wolfe et al. | 600/534 |
| 2010/0286567 A1 | 11/2010 | Wolfe et al. | 600/587 |

\* cited by examiner

SNORING TREATMENT

CROSS REFERENCE TO RELATED APPLICATIONS

This application is related to the following U.S. patent applications:

Ser. No. 12/436,615, entitled Accelerometer Based Health Sensing, filed on May 6, 2009;

Ser. No. 12/392,889, entitled Sudden Infant Death Prevention Clothing, filed on Feb. 25, 2009;

Ser. No. 12/436,462, entitled Elderly Fall Detection, filed on May 6, 2009;

Ser. No. 12/392,913, entitled Microphone for Remote Health Sensing, filed on Feb. 25, 2009; and Ser. No. 12/400,488, entitled Noise Cancellation for Phone Conversation, filed on Mar. 9, 2009. The contents of each of the above listed applications are hereby incorporated by reference herein in their entireties.

BACKGROUND

Several health related conditions or occurrences may have indicators that reflect a measurable factor such as motion or lack of motion. For example, for sleep apnea, a sleep disorder where an individual stops breathing for an extended period of time, the indicator may be a lapse in breathing. As such, the individual's chest and/or abdomen may fail to move during this period of time. Similarly, motion may also be related to the non-breathing infant suffering from Sudden Infant Death Syndrome (SIDS). An additional example of a health related condition or occurrence relating to motion is an injury to an elderly person caused by falling.

While some indicators may reflect motion, other indicators may reflect an additional or alternative measurable factor. The most basic vital signs are pulse, blood pressure, body temperature, and respiratory rate. As discussed above, respiratory rate may reflect motion. However, while pulse may be based at least in part on the motion of the heart, it is often sensed using sound sensing instruments. Blood pressure may also often be sensed using a sound instrument together with a pressure cuff and body temperature is independent of motion altogether. Additionally, with respect to SIDS, an indicator of a possibly dangerous condition may be when an infant is sleeping on their stomach. That is, where infants are positioned on their back when sleeping, the number of occurrences of SIDS tends to decrease. Thus, an indicator relating to SIDS may reflect a measurable factor such as the sleep position of the infant.

BRIEF DESCRIPTION OF THE FIGURES

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several examples in accordance with the disclosure and are, therefore, not to be considered limiting of its scope, the disclosure will be described with additional specificity and detail through use of the accompanying drawings.

DETAILED DESCRIPTION

Figure 1:
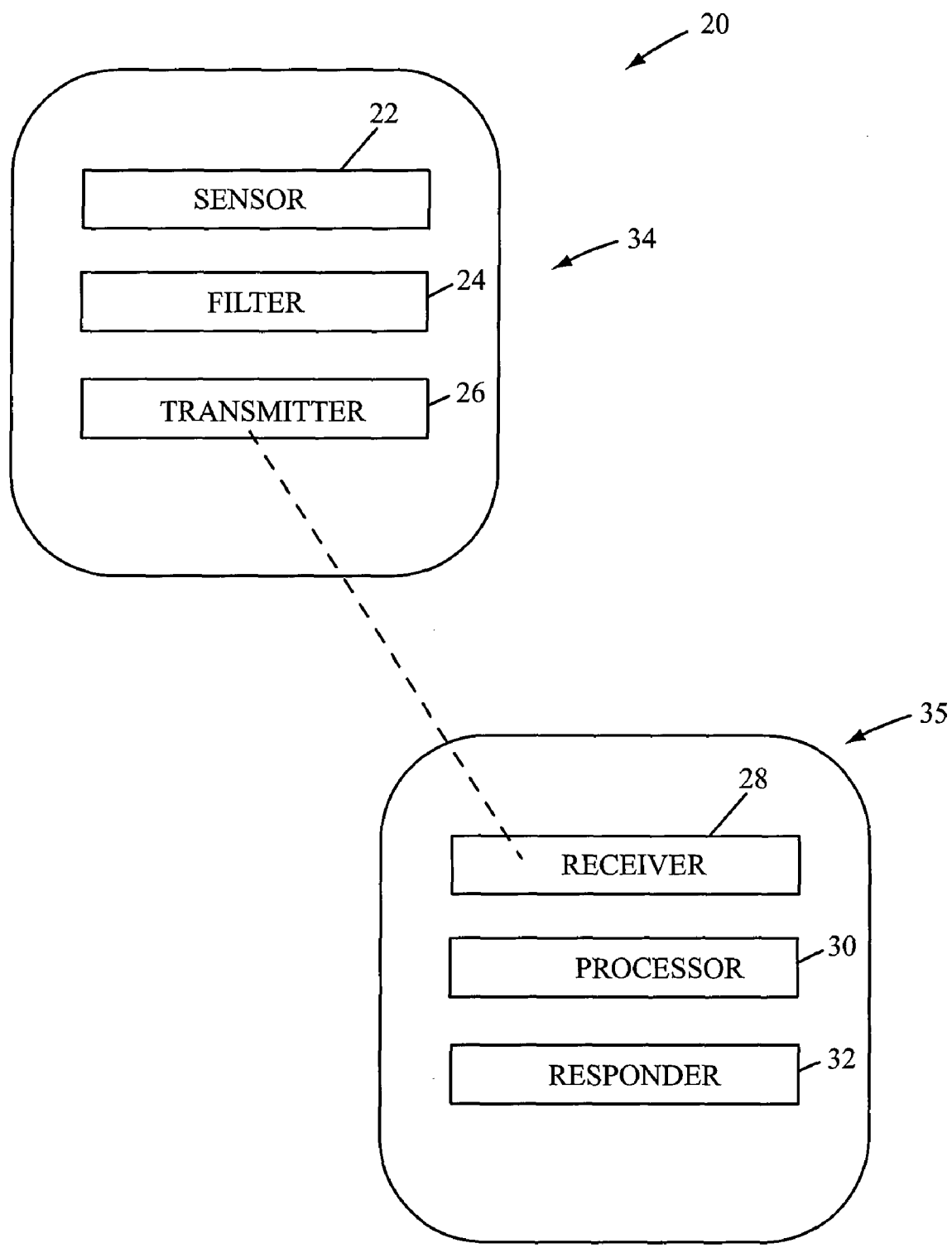
FIG. 1 is a schematic diagram of a system for monitoring indicators of health related conditions or occurrences, arranged in accordance with some examples of the present disclosure.

The following description sets forth various examples along with specific details to provide a thorough understanding of claimed subject matter. It will be understood by those skilled in the art, however, that claimed subject matter may be practiced without some or more of the specific details disclosed herein. Further, in some circumstances, well-known methods, procedures, systems, components and/or circuits have not been described in detail in order to avoid unnecessarily obscuring claimed subject matter.

In the following detailed description, reference is made to the accompanying drawings, which form a part hereof. In the drawings, similar symbols typically identify similar components, unless context dictates otherwise. The illustrative examples described in the detailed description, drawings, and claims are not meant to be limiting. Other examples may be utilized, and other changes may be made, without departing from the spirit or scope of the subject matter presented herein. It will be readily understood that the aspects of the present disclosure, as generally described herein, and illustrated in the Figures, may be arranged, substituted, combined, separated, and designed in a wide variety of different configurations, all of which are explicitly contemplated herein.

Monitoring indicators of health related conditions may allow certain conditions to be treated and may facilitate intervention where necessary. Additionally, monitoring the indicators may facilitate prompt response to certain health related occurrences. Manual monitoring of these indicators may be difficult due to the subtle nature of these indicators together with unpredictable and sometimes untimely health related conditions or occurrences.

The following detailed description relates to sensing measurable factors associated with indicators of health related conditions or occurrences and further relates to actions that may be taken in response to those measurements. The description includes discussion of sensors, for sensing several measurable factors, and data acquired by the sensors. The description further includes a discussion of a system that may sense measurable factors and acquire data, provide a sensor signal with data to a filter, filter the data provided by the sensor, provide a filter signal to a transmitter, and transmit an associated transmission signal. The system may also receive a transmitted signal, process the transmitted signal, and take or prompt a responsive action. For example, in the case of snoring, the system may sense motion associated with the sleep partner of a snorer, provide a sensor signal to a filter which may filter the result and transmit a signal when the result is indicative of sleep irritation. In turn, the system may receive the transmitted signal and process the transmitted signal depending on the goals and set-up of the particular system. That is, again in the case of snoring, the system may process the transmitted signal by activating a mitigation device involving emitting a sound which attempts to cancel the sound of the snorer.

More particularly, in some examples the system may include an accelerometer type sensor adapted to sense measurable factors such as the motion or the position of a user. In an example, the system may include a microphone type sensor adapted to sense sound. The system may include a filter in the form of a processor for analyzing the data from the sensor to determine if an indicator has been detected. A transmitter may be included for transmitting a signal. The system may include a receiver for receiving the transmitted signal and an additional processor. The additional processor may determine what type of responsive action may be appropriate and may further initiate or prompt that action. These actions may include stimulating the user to interrupt an indicator episode, notifying a third party to intervene, monitoring the user, or mitigating the indicator episode. The sensor or transmitter may be provided for placement at separate locations.

Referring now to FIG. 1, a schematic diagram of a system 20 for monitoring indicators of health related conditions or occurrences is shown, according to some examples of the present disclosure. The system 20 may include one or more of a sensor 22, a filter 24, and a transmitter 26. The system 20 may also include a receiver 28, a processor 30, and a responder 32. The sensor 22, filter 24, and transmitter 26 may be provided as a health-sensing device 34 of the system. Further, the receiver 28, processor 30, and responder 32 may be provided as a health-action device 35 of the system 20. The health-sensing device 34 and health-action device 35 may be provided by the same entity or may be separately provided while being configured to communicate with each other. Also, the various functions and features of the individual functional components (e.g., 22, 24, 26, 28, 30, and 32) may be combined into one or more integrated solutions, or separated into additional functional components as may be desired in a particular implementation.

The sensor 22 may include one or more individual sensors of any variety. In some examples, the sensor 22 may be adapted to sense measurable factors reflecting indications of health related conditions or occurrences. For example, the sensor 22 may be a thermometer, an automatic blood pressure sensor, or a pulse sensor. In another example, the sensor 22 may be an accelerometer. In still further examples, the sensor 22 may be a microphone or an ultrasound sensor. In still another example, the sensor 22 may be a rapid eye movement sensor. In yet another example, the sensor 22 may be a blood sugar sensor or an air flow sensor. The type of sensor 22 used, may be based at least in part on the type of health related condition or occurrence that the system 20 is intended to address. Additionally, multiple sensors 22 may be included to address several conditions or occurrences at any given time. Additionally, several levels of sophistication may be available for each type of sensor 22. For example, several levels of precision, accuracy, and detail may be available depending on the type and quality of the sensor 22 selected for use. Moreover, the sensor 22 may provide continuous or periodic signals to the filter 24 or the signals may be based at least in part on the circumstances of what is being sensed and what values are being sensed.

An accelerometer type sensor 22 may sense changes in velocity and thus may be used to sense motion. Such a sensor 22 may be appropriate for health related conditions such as sleep apnea, Sudden Infant Death Syndrome (SIDS), heart conditions, pregnancy, or any other health condition related to motion. As discussed briefly above, sleep apnea may be indicated by a lapse in breathing, which may cause motion of the chest and/or abdomen to stop. As such, the application of an accelerometer to the chest and/or abdomen of a person suffering from sleep apnea may allow for sensing the associated breathing patterns. Regarding SIDS, while the actual cause may be unknown, it may involve a lapse in breathing and an accelerometer may be used in a similar manner as with sleep apnea. With respect to heart conditions, motions related to a heartbeat may be sensed in several locations on the human body allowing for sensing of patterns including heart arrhythmias. Regarding pregnancy, the motions associated with uterine contractions may also be appropriately sensed with an accelerometer by placing it on the surface of the abdomen to sense the motion of the abdomen and reflect the contraction pattern of the uterus.

In addition to the health related conditions discussed above, an accelerometer may also be appropriate for health related occurrences such as falling down, blunt force trauma, or any occurrence involving a change in speed or direction. When a person falls, they may experience an initial acceleration followed by additional acceleration until they encounter the ground or other object, at which point they may experience a rapid deceleration or negative acceleration. As such, the occurrence of a fall or series of falls may be sensed by an accelerometer positioned on the body and may be particularly useful for the elderly. Similarly, an accelerometer may be used to sense occurrences related to blunt force trauma. This may be relevant for car accidents, abuse, or similar situations.

In addition to sensing motion, an accelerometer may sense position in the absence of motion. An accelerometer may be sensitive to gravitational forces depending on its orientation relative to the surface of the earth. As such, an accelerometer may also be used to sense the position of a user where the orientation of the accelerometer is dependent on the position of the user. This may facilitate use of an accelerometer for monitoring infants for SIDS. It has been shown that infants positioned on their back while sleeping may be less likely to be subject to SIDS. An accelerometer thus may be used to sense this sleep position by securing the accelerometer to the infant such that the orientation of the accelerometer changes as the infant's sleep position changes allowing the accelerometer to sense when the infant may be face down.

A microphone may also be used as a sensor 22 to sense sound and may be appropriate for health related conditions such as snoring, heart disease, or any other condition involving the emission of sound. Like an accelerometer, a microphone may be used to sense heartbeats from several locations on the body, allowing for sensing of patterns including heartbeat arrhythmias. With respect to snoring, a microphone may be used to sense the volume, frequency, pattern or any other aspect of the sound relevant to the snoring condition.

Continuing with the discussion of FIG. 1, a filter 24 may be provided and may be configured to receive a sensor signal from a single sensor 22. In other examples, the filter 24 may be programmed to monitor more than one incoming sensor signals from one or more sensors 22. The sensor signal may include one or more digital signals or analog signals, which may carry data from the sensor 22 to the filter 24 for further analysis or processing. In one example, a basic signal filter (e.g., a digital filter or an analog filter) may be capable of determining whether a specific condition exists or does not exist. That is, the sensor 22 may provide one sensor signal to the filter 24 for one condition and an alternative sensor signal for another condition. The filter 24 may wait for one or the other sensor signal and then may communicate a corresponding filter signal to the transmitter 26. In some examples, the filter 24 may be omitted, for example, where the sensor 22 is adapted to provide a sensor signal when a specific condition exists. In another example, the filter may be in the form of a processor (e.g., a digital signal processor (DSP), a microcontroller, a micro-processor, an analog signal processor, field-programmable gate arrays (FPGAs), an application specific integrated circuit (ASIC), etc.), and may be used to provide additional analysis of the sensor signal. That is, the sensor 22 may provide a sensor signal involving a value for comparison to a threshold value defined relative to certain health related conditions discussed below. Alternatively, the sensor 22 may provide a series of sensor signals to be considered together. For example, the series of sensor signals may define a pattern where gaps or inconsistencies in the pattern may be analyzed.

Based at least in part on the result of analysis conducted by the filter 24, the filter 24 may communicate a filter signal (i.e., a filtered version of the signal received from sensor 22) to the transmitter 26. The filter signal may take one form or a combination of forms. In one example, the filter signal may reflect that an indicator has been detected. In another example, the filter signal may be an indication signal together with the data received from sensor 22. In still another example, the filter signal may be an indication signal together with the data received from the sensor 22 and any additional information regarding the indicating episode. This additional information may include interpretive information such as severity, duration, or type of condition or occurrence. In yet another example, the filter signal may be a continuous data stream reflecting the continuing values sensed by the sensor 22. In still another example, the filter signal may include instructions relating to the action to be taken with respect to the several types of data. In some examples, the filter 24 may be either omitted or incorporated into the sensor 22 and the filter signal may be provided by the sensor 22 to the transmitter 26. In still another example, the filter signal may take the form of a continuous or periodically sent beacon signal for assuring that communication has not been lost due to reduced proximity, power loss, or other conditions.

In the case of sleep apnea, the filter 24 may receive a sensor signal from the sensor 22 reflecting the breathing pattern of a user. The sensor signal may have gaps where the user pauses between breaths. The filter 24, in this example, may be a processor capable of timing the length of the gaps and comparing the length of the gap to a threshold value. A gap in breathing that exceeds approximately 10 to 20 seconds may be considered an apnea. Alternatively, other lengths of time may be used and may be customized to a user. As such, the processor may communicate a filter signal to the transmitter 26 when a selected threshold value is exceeded. The filter signal may be an indication signal reflecting a likelihood that an apnea has occurred. In another example, the filter signal may be an indication signal together with the data relating to the breathing pattern surrounding the apnea. In another example, the filter signal may also include data relating to the apnea such as how long breathing lapsed, how many apneas per hour are occurring, and the like.

The above described process may also be performed by the filter 24 when an infant is being monitored for the breathing related aspects of SIDS. Where the infant is being monitored for the sleep position aspects of SIDS, the filter 24 may have alternative functionality. The filter 24 may receive a sensor signal from the sensor 22 reflecting the sleep position of the infant. This may be a signal with a varying scale or it may be a signal reflecting that the infant may be on his/her back or on his/her stomach. Where the sensor 22 is limited to a sensor signal reflecting that the infant is on his/her back or stomach, the filter 24 may be configured to do substantially nothing unless and until the sensor signal is received reflecting that the infant is on his/her stomach. At that point, the filter 24 may communicate a filter signal to the transmitter 26. This example may be simplified where the sensor 22 does not send a sensor signal unless the infant is on his/her stomach. In that example, the filter 24 may be configured to initiate a filter signal to the transmitter 26 when the filter 24 receives a sensor signal from the sensor 22. Alternatively, the filter 24 may be eliminated and the sensor 22 may send a sensor signal to the transmitter 26. In the above examples, the signal (whether a filter signal or a sensor signal) sent to the transmitter 26 may take several forms and may include on or more levels of data. This may be dependent on the level of sophistication of both the sensor 22 and the filter 24 and further dependent on the goals associated with using the system.

In the case of falls, the filter 24 may receive a sensor signal from the sensor 22 reflecting the level of force being experienced by the user. In some examples, this level of force may be in comparison to that of gravity and thus may be presented as a certain number or fraction of G forces or G's. In some other examples, the level of fall may be based at least in part on a physiological model including an analysis of peak acceleration, total energy, and direction. As such, when the sensor signal reflects that the G force has exceeded a threshold limit or the model reflects a certain level of likelihood of fall or injury, the filter 24 may communicate a filter signal to the transmitter 26. In some examples, the filter signal may be an indication that a fall has likely occurred. In some other examples, the filter may define the fall as meeting a certain level. That is, a low level may indicate likelihood of fall, or light fall. An intermediate level may indicate a higher likelihood of fall, or medium fall. A high level may indicate a high likelihood of fall, or hard fall. In each level, a specific response may apply. As such, the filter signal may be adapted accordingly. In additional examples, the filter signal may include additional data relating to the level of G force experienced and may include some data regarding the history of falls.

The filter 24 may have a similar role in uses of the system for monitoring heart conditions. The filter 24 may receive a sensor signal from the heart sensor and may be programmed to recognize several known heart arrhythmias or may be a more basic filter limited to recognizing only life threatening heart conditions. In either case, the filter 24 may be configured to respond to heart arrhythmias based at least in part on specific instructions related to each or more generic instructions related to all arrhythmias. Having recognized a heart arrhythmia or other known problem, the filter 24 may communicate a filter signal to the transmitter 26. In some examples, the filter 24 may continually send a filter signal to the transmitter 26 with the results received by the sensor 22 and also continue to monitor the sensor signal from the sensor 22 for problems.

Similarly, with respect to contractions during pregnancy, the filter 24 may receive a sensor signal from a contraction sensor and may interpret the data with respect to frequency and/or magnitude. In this example, while high frequency and/or high magnitude may trigger the filter 24 to communicate a filter signal to the transmitter 26, the filter 24 may also send a continuous filter signal to the transmitter 26 reflecting the continuing data and thus the contraction pattern received from the contraction sensor.

In other examples, the filter 24 may also be adapted for use in monitoring or treating snoring. The filter 24 may receive a sensor signal from a sound sensor and may measure the level of the sound to determine if it exceeds a threshold level. As discussed with respect to other conditions, this example may include sending a range of possible filter signals to the transmitter 26 including an indication of snoring, the decibel of the snoring, and/or a continuous signal reflecting the snoring pattern. In some examples, the filter 24 may receive a sensor signal from a motion sensor or other sensor positioned on or around a sleep partner. In this example, the sensor positioned on or around the sleep partner may be adapted to sense sleep partner irritation. As such, the filter 24, in this example, may be adapted to rely on both the sound sensor and the motion sensor to determine what action to take. That is, if the snoring is loud or continuous, the filter 24 may send a filter signal to the transmitter to trigger a sound canceling device or to trigger a stimulation device. The filter 24 may receive information from the motion sensor as to the irritation level of the sleep partner. As such, when the snoring is not loud or continuous or otherwise bothersome, the filter 24 may still send a filter signal to the transmitter 26 to trigger a sound canceling device or to trigger a stimulation device. In an example, the filter 24 may not send a filter signal to the transmitter 26 if no sound is being detected or the sound is low. That is, if the sleep partner is just restless, a filter signal may not be sent.

With continued reference to FIG. 1, the transmitter 26 of the system 20 may include any known device for transmitting information. This may include any wired transmitter or wireless transmitter. The transmission may be in digital or analog form and may be a radio transmission or other type of transmission. Any suitable radio transmitter, low voltage communication device, wireless device, or any communication device known in the art may be used. In some examples, the transmitter 26 may be a radio packet, short distance communication system. In other examples, the transmitter 26 may be adapted for longer distance communication.

Accordingly, the receiver 28 of the system 20 may be any known device for receiving information. The receiver 28 may be chosen at least in part to correlate with the type of transmitter 26 used. As such, the receiver 28 may include any wired receiver or wireless receiver. Moreover, the receiver 28 may be adapted to receive the transmission from the transmitter 26 and communicate the associated information to the processor 30 with a receiver signal. The transmitter 26 may include an antenna of any variety. In an example, the antenna may be a strip-line antenna. In some other examples, the antenna may be a coil-type antenna.

Still referring to FIG. 1, the processor 30 may receive the transmitted signal from the receiver 28. As with the filter 24, the processor 30 may be chosen at least in part based on the goals and needs of the system. The processor 30 may be triggered by the receiver signal to complete a single specific task. In an example, having received a receiver signal, the processor 30 may drive a device in response. In some other examples, the processor 30 may separate the incoming transmitted data into categories relating to the action to be taken. Some of the data may be intended for storage or display, some may be intended to trigger a stimulus, notification, or mitigation response, and some may require interpretation prior to moving on to these tasks. As such, the processor 30 may perform several tasks corresponding to the form of the data it receives and the actions that need to be taken.

Concluding the discussion of FIG. 1, the responder 32 may include several options for devices adapted to respond to the information gathered by the sensor 22. The responder 32 may include a database for storing the data for later analysis. The responder 32 may also include a display for displaying the data for real time analysis or monitoring. In one example, the responder 32 is a stimulation device for stimulating the user. In another example, the responder 32 may be a notification device for notifying a third party. In another example, the responder 32 may be a mitigating device for mitigating a given situation.

For example, the responder 32 may include a computer with a graphics display and a hard drive or other database structure. Alternatively, a stimulation device in the form of a vibratory or alarm type device may be included. Alternatively, a similar device may be included to notify a third party. The notification device may include a light up display, alarm, or vibratory device. Alternatively, a mitigating device may include any device adapted to assist a user or other person in coping with a health condition or occurrence.

In the case of sleep apnea, a non-breathing episode may be interrupted by a stimulus which arouses a user sufficiently for them to begin breathing again. Alternatively, a notification may be provided to a third party. In the case of SIDS, a parental monitor may be activated to notify the parent of a life threatening or otherwise potentially dangerous condition such as a non-breathing infant or an infant that may have rolled onto his/her stomach. In the case of heart conditions, the responder 32 may include a device for stimulating the user and may shock their heart to attempt to correct an arrhythmia. In an example, the responder 32 may include a database for storing a continuous stream of heartbeat history. The responder 32 may also include a continual display of the heartbeat on a computer display or other display to allow the heart to be monitored. In the case of a user who has fallen, the responder 32 may include a notification device for notifying a nurse at the user's nursing home, or a family member, that assistance may be needed. In the case of snoring, a stimulation similar to that discussed above regarding apnea may be included. In another example, a mitigation device such as a sound cancellation device may be used to cancel out the sound of the snoring in an effort to comfort those around the snoring person.

Figure 2:
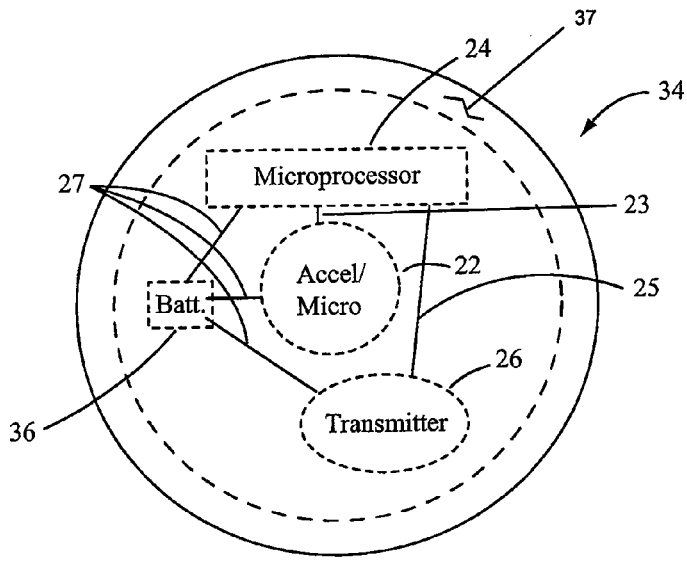
FIG. 2 is a top schematic view of the components of a health-sensing device, arranged in accordance with some examples of the present disclosure.

FIG. 2 is a top schematic view of the components of a health-sensing device 34, arranged in accordance with some examples of the present disclosure. Health-sensing device 34 may include a sensor 22, a filter 24, and a transmitter 26 and thus may include three elements of the system shown in FIG. 1. In other examples, more or fewer elements may be provided. In an example, the sensor 22 may be an accelerometer, microphone, or any combination of previously described sensors. In an example, the filter 24 may be a microprocessor and the transmitter 26 may be a radio transmitter. Additionally shown is a power source 36 (e.g. a battery) for powering the several elements of the health-sensing device 34. Other sensors 22, filters 24, and transmitters 26 described herein or otherwise may also be used in a health-sensing device 34 like the one described here and are within the scope of the present disclosure.

In the example shown in FIG. 2, the sensor 22 may be coupled to the filter 24 with an information bus 23 for carrying information sensed by the sensor 22 in the form of a sensor signal to the filter 24. Additionally, the filter 24 may be coupled to the transmitter 26 with an additional information bus 25 for carrying information to the transmitter 26 in the form of a filter signal. The power source 36 may be included to power one or several of the included elements and may be coupled to each of the elements 22, 24, and 26 as shown with a power wire or cord 27. In an alternative embodiment, the power source only powers the filter 24, which may power the sensor 22 and the transmitter 26 by including power in conjunction with the data buses 23 and 25. The power source 36 may be a battery or series of batteries and may be capable of being turned on and off. In one example, the battery may be a zinc based battery and may be a Zinc/Air battery. In some other examples, the battery may be a Lithium-ion based battery, a Nickel Cadmium based battery, or a Nickel Metal Hydride.

The example of FIG. 2 may include a substrate 37 for positioning of the elements of the health-sensing device. The substrate 37 may be a flat and/or flexible material for securing the elements of the device. As such, the substrate 37 may be silicon-based, ceramic-based, glass-type, quartz-type or any other reasonable material for positioning and of the elements. In some examples, the substrate 37 may be a high-performance plastic such as polyimide or Polyetheretherketone (PEEK) film. In other examples, polyester may be used, for instance with silver screen printed circuits. In other examples, a variety of potting materials may be used such as an epoxy resin. The substrate 37 may also include an enclosing structure. This enclosing structure may be in the form of a patch and may include a shielding structure. For example, in the case of a radio frequency transmitter and/or receiver, the patch may include a shielding structure to prevent radio frequency interference (RFI). The patch may be a relatively soft flexible material or it may be a more rigid material. The patch may be made from several materials including, but not limited to nylon, cotton, plastic or any other material appropriate for use in contact with the body or clothing. The material of the patch may be waterproofed with a coating or be naturally waterproof. Depending on the nature of the patch (e.g. flexible or rigid) the elements of the device may be enclosed within the patch in an envelope type structure or the elements may be provided on the surface of a substrate 37. In one example, the elements of the device may be provided on the surface of a silicon based substrate 37, the substrate 37 further including an enveloping waterproofed nylon material in the form of a patch. Several orientations of the elements within the patch may be used, based at least in part on electrical connections between the elements and physical placement within the patch. Depending on the type of sensor 22 and the condition for which it is being used, the sensor 22 may be located near the surface of the patch that is located adjacent to the user so as to reduce relative movement, or other interference, between the surface of the user and the sensor 22.

Figure 3:
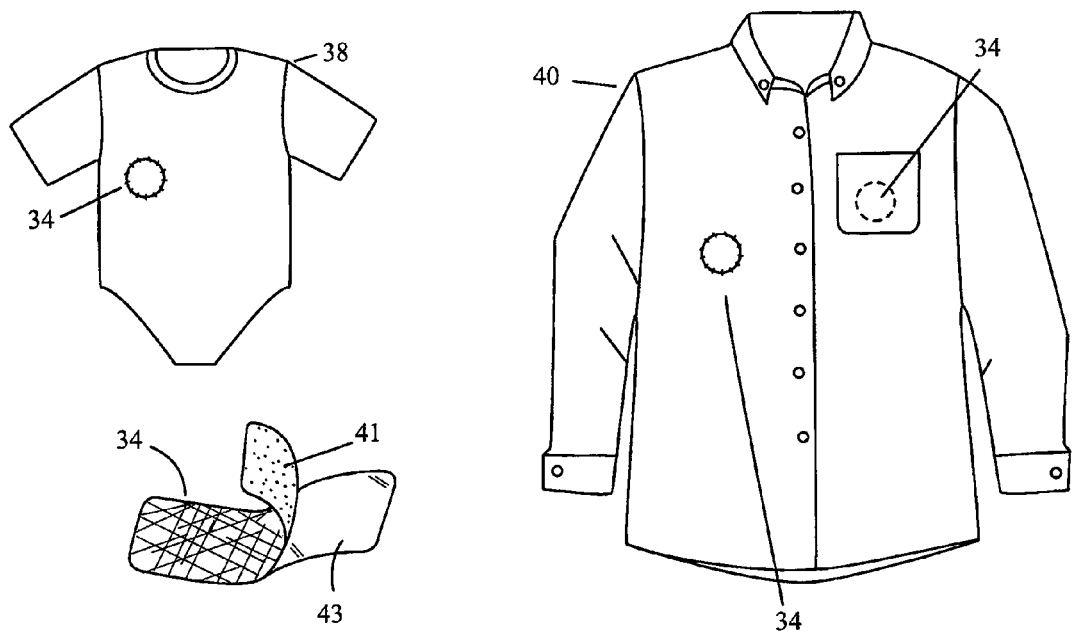
FIG. 3 is a diagram of a health-sensing device incorporated into clothing, arranged in accordance with some examples of the present disclosure.

FIG. 3 is a diagram of a health-sensing device incorporated into clothing, arranged in accordance with some examples of the present disclosure. As shown, the patch may have an affixing element such as a peel and stick bottom surface 41 for adhering the patch to a user, where a protective layer 43 over the adhesive may be removed prior to applying the patch. In one example, the patch may include a bio-adhesive for securing the patch directly to the skin of a user. This bio-adhesive may have an adhesive value so as to make removal difficult. In the case of infants or elderly users who may suffer from dementia or otherwise have a tendency to remove the device, the patch may be securely affixed to the user and may not be easily removed. In an example, the patch may be located in a hard to reach location to make removal difficult. The affixing element may be an attachment surface for repeated application such as a hook and loop surface with a complementary hook and loop surface worn by the user. In still another example, the affixing element may include self securing straps for wrapping around a portion of a user's body for securing the patch between the straps and the surface of the user's body. The straps may have several openings for receiving corresponding protrusions for adjustability or may be self-secured with buttons, hook and loop, buckles, or other means known in the art.

Referring again to FIG. 3, in an example, the affixing element of the health-sensing device 34 may be adapted to incorporate the device 34 into clothing. In some examples, the device 34 may be configured substantially as shown and described with respect to FIG. 2. In one example, the device 34 may be sewn or otherwise affixed to baby clothing 38 such as a sleeper, a shirt, a one size body suit or other attire worn by a baby. In another example, the patch may be sewn or otherwise affixed to adult clothing 40. The health-sensing device 34 may be otherwise secured to clothing through the use of buttons, fabric glue, or other methods known for fastening devices to clothing. In some examples, the health-sensing device 34 may not be fixedly secured, but may be placed in a pocket of a shirt or other clothing article.

The sensors or other elements of the present disclosure may be micro-electro-mechanical systems (MEMS) devices. That is they may incorporate integrated circuit technology with microfabrication in the form of micromachining. Alternatively, the sensors or other elements may be made from more or less sophisticated technologies.

Figures 4A, 4B:
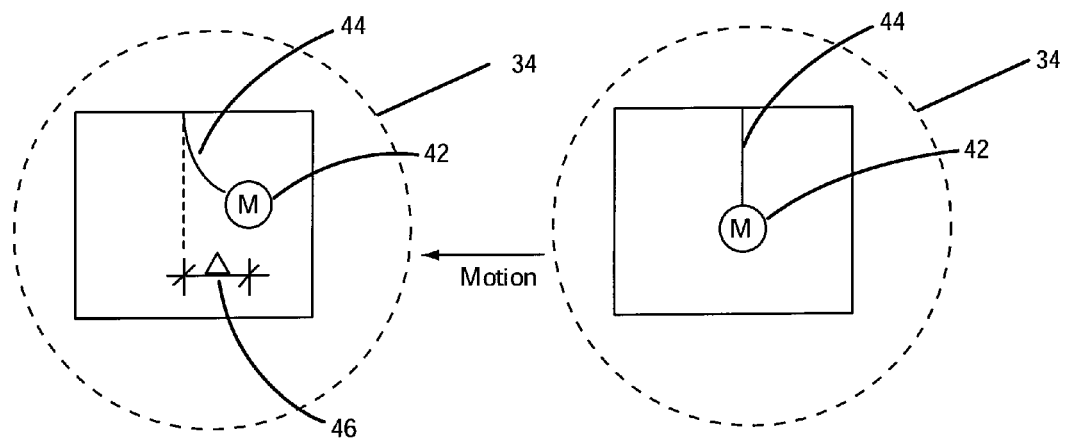
FIGS. 4A and 4B are schematic diagrams of an accelerometer within a health-sensing device, arranged in accordance with some examples of the present disclosure.

FIGS. 4A and 4B are schematic diagrams of an accelerometer within a health-sensing device 34, arranged in accordance with some examples of the present disclosure. The accelerometer disclosed herein may sense motion associated with the user. An accelerometer may function by monitoring the effect on a mass 42 positioned on the end of a cantilevered deflectable resistance. That is, the mass 42 may be held in place with a deflectable resistance 44 as shown in FIG. 4A and may otherwise be free to oscillate. When the accelerometer is moved, for example, in the direction of the arrow from the FIG. 4A position to the FIG. 4B position, the mass 42 may have a tendency to stay in place relative to the accelerometer. The motion of the accelerometer, thus, may cause a deflection 46 in the deflectable resistance 44 for any given accelerative motion. The deflection 46 may be a measurable distance and the deflectable resistance 44 may have certain known section properties. As such, the deflection causing force acting on the mass 42 may be calculated from the deflection 46 and the section properties using conventional beam theories. With a known deflection causing force and a known mass, an acceleration may then be calculated using Newton's second law of motion, F=ma. (e.g. a=F/m) Where the accelerometer is affixed to a user, the acceleration of the accelerometer may be assumed to match that of the user.

The accelerometer may be secured within a health-sensing device 34 to reduce the effect of relative motion between the accelerometer and the user. Where the health-sensing device 34 is flexible, the accelerometer may be located near the affixing surface. Where a relatively rigid device is used and the accelerometer is secured therein, more options for the location of the accelerometer may be available. In various examples, the accelerometer may take the form of a basic spring based accelerometer, an E-transformer accelerometer, or any other accelerometer. The accelerometer may be designed and calibrated based at least in part on a specific health condition. In cases of small accelerations, such as heartbeats and contractions, a relatively sensitive accelerometer may be used. In contrast, where falls or sudden involuntary motions are being monitored, a relatively less sensitive accelerometer may be used.

Figures 5A, 5B:
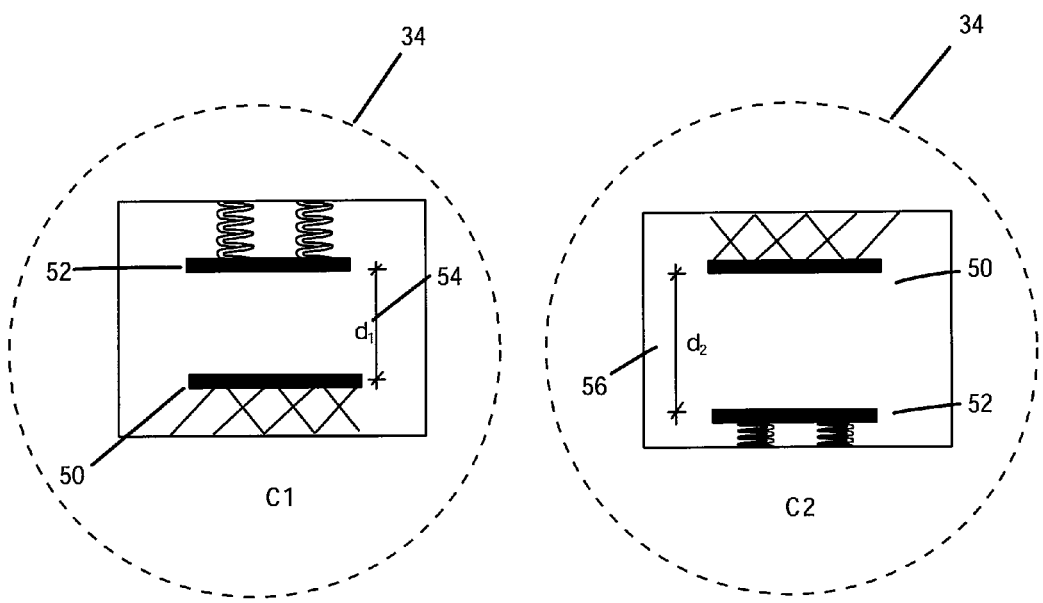
FIGS. 5A and 5B are schematic diagrams of a capacitor-based accelerometer within a health-sensing device, arranged in accordance with some examples of the present disclosure.

FIGS. 5A and 5B are schematic diagrams of a capacitor-based accelerometer within a health sensing device 34, arranged in accordance with some examples of the present disclosure. The accelerometer within the health-sensing device 34 may take the form of a variable capacitance device. Capacitors may store energy in an electric field between a pair of conductor plates. The capacitance value of a capacitor may be affected by several factors, such as the area and materials of the conductive plates, the distance between the conductive plates, and a dielectric value associated with the gap between the conductive plates. As used herein, the variable capacitance device may sense motion or orientation by having a conductor plate spacing that varies depending on the orientation or motion of the device. As such, the capacitor may be affixed to a user causing the orientation or motion of the user to affect the capacitance value of the variable capacitance device.

For example, the variable capacitance device may be designed with two plates spaced apart from each other. In one example as shown, one of the plates may be a rigidly supported plate 50 and the other plate may be a flexibly supported plate 52 positioned above the rigidly supported plate 50. As shown in FIG. 5A, when the device is in an upright position (e.g., rigidly supported plate 50 on the bottom, flexibly supported plate 52 on the top) the device may have a first capacitance value, C1, that is determined by a first distance 54, d1, between the plates 50 and 52. However, when the device is in the inverted position, as shown in FIG. 5B (e.g., rigidly supported plate 50 on the top, flexibly supported plate 52 on the bottom), the force of gravity may cause the flexibly supported plate 52 to move away from the rigidly supported plate 50 and may cause the device to have a second capacitance value, C2, that may be different from the first capacitance value, C1. Since the distance 56, d2, between the plates 50 and 52 may be greater in the inverted position than in the upright (or non-inverted) position, and since capacitance value may be inversely proportional to the distance between the plates, the second capacitance value (C2) may be smaller than the first capacitance value (C1). The orientation of the conductor plates 50, 52 may be reversed such that the upright position may be defined by the flexibly supported plate 52 being below the rigidly supported plate 50.

The variable capacitance device may be designed and calibrated with respect to a specific health condition. For example, in the case of SIDS, where the concern relates to an infant rolling from their back to their stomach, an acceleration shift from 1 G to −1 G is reflected. As such, the sensitivity may be relatively low. That is, the support for the flexibly supported plate 52 may be relatively stiff. However, where a similar device is also being used to sense breathing or other relatively small accelerations, the sensitivity may be relatively high and the support for the flexibly supported plate 52 may be relatively flexible. Other known and later developed accelerometer designs may be appropriate for use in the devices described herein.

Similarly, the microphone may be a micro-electro-mechanical systems (MEMS) microphone. As such, the microphone may take the form of a variable capacitance circuit with a capacitance value determined by the spacing between a diaphragm and a back plate. Sound, which generally may be described as a moving air pressure wave, may cause the diaphragm to vibrate such that the capacitance value changes in the circuit due, at least in part, to the changing position of the diaphragm relative to the back plate. The sound may thus be transformed into an electrical signal via the variable capacitance circuit. Alternatively, the microphone may be an electret condenser type of microphone (ECM).

Figure 6:
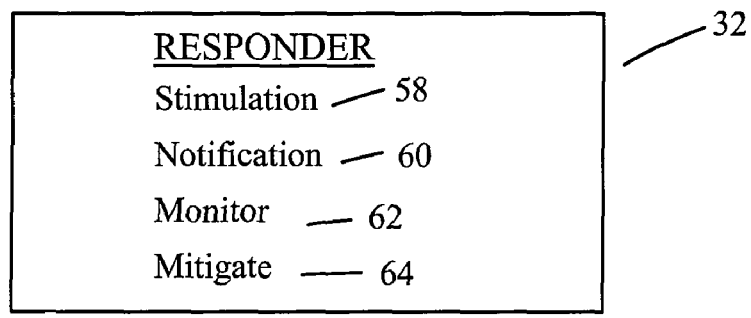
FIG. 6 is a diagram illustrating actions taken in response to a signal, in accordance with some examples of the present disclosure.

FIG. 6 is a diagram illustrating actions taken in response to a signal, in accordance with some examples of the present disclosure. The example actions may include stimulation, notification, monitor and mitigate. The responder 32 of a system as described with respect to FIG. 1 may include one or more of a stimulation device 58 to provide the stimulation action, a notification device 60 to provide the notification action, a monitoring/storage device 62 to provide the monitor action, and a mitigation device 64 to provide the mitigate action.

Regarding the stimulation device 58, several health conditions may lend themselves toward this action. For example, sleep apnea, SIDS, heart conditions, contractions, diabetes, and snoring may be appropriately treated, at least temporarily, by stimulating the user. For the conditions relating to breathing, several methods of stimulation may be used such as sounding an alarm, a tone, or other audible stimuli in close proximity to the user. These devices may be positioned on or around the user so as to stimulate them when activated. In other examples, a vibratory or other mechanical stimulus such as a poking, prodding, shaking, or squeezing device may be used. These devices may be attached to the user, placed beneath the user, or otherwise positioned to physically contact and arouse the user. In the case of heart arrhythmias, audible or mechanical agitation methods may be sufficient to arouse the patient and correct a minor arrhythmia. However, in some examples, the stimulus may involve shocking the user in an attempt to correct the arrhythmia. This may occur through the use of patches or other electrode-type devices positioned on the abdomen wall, which are configured to deliver an electric current with a shocking voltage similar to a defibrillation or cardioversion device. In the case of contractions, the stimulus may actually be an injection or other dosing intended to prevent further contractions. Regarding diabetes, a stimulus similar to those described for breathing conditions may be sufficient to arouse a diabetic suffering from low blood sugar allowing them to correct the deficiency by eating, drinking, or other known techniques. In the above cases, the stimulation action may interrupt and may treat a given sensed condition or occurrence.

Regarding the notification device 60, several health related conditions or occurrences may lend themselves toward a notification action. For example, falling, heart conditions, and SIDS may lend themselves to notification of someone who can assist the user. An elderly person in a nursing home may require assistance from staff after a fall. A light on a light board or in the hallway may be activated to trigger the staff. In another example, a notification on a computer screen may be provided. Similarly, a user suffering from a heart condition may need hands on support to treat a heart arrhythmia or myocardial infarction. As such, similar notifications may be made to hospital staff, family members, or an emergency response service. In the case of SIDS, whether breathing has stopped or the infant has rolled onto their stomach, a notification of parents may be appropriate and may include a sound alarm or other notification allowing the parent to attend to the infant.

In addition to the notification devices mentioned, additional notification devices may be positioned more proximal to the user. For example, regarding falling, a device proximally located to the user may notify the user triggering them to tell a monitoring party that they are not in need of assistance. That is, the level of acceleration sensed by the sensor may be relatively low reflecting a mild fall or that the health-sensing device had been inadvertently bumped. A device may be positioned on the user or proximally to the user and may light up or otherwise notify the user that their device has indicated a fall. If the user is not in need of assistance the user may notify a third party that no assistance is needed. In one example, a notification device may be positioned on the health-sensing device positioned on the user. This example may also include a button or other actuatable element allowing the user to notify the third party that they do not need help by pushing the button or other actuatable element and triggering a transmission signal. In another example, a user with a heart condition may be notified of an irregular heart beat prior to them being able to feel the condition. This may allow the user to sit down or otherwise be proactive in addressing a given condition or occurrence. Several devices for notifying others are known and are within the scope of the present disclosure. These may include pagers, computers, cell phones using text messages, and other notification devices.

Regarding storing/monitoring devices 62, many of the conditions may be appropriate for this action. In some examples, a stored or monitored history may be relevant to analyzing a condition, occurrence, or series of occurrences. One suitable action may involve storing the sensed data, or the existence of a condition or occurrence, for later reference and analysis. Additionally, a continuous display may be appropriate for live monitoring and analysis of a given condition.

Regarding mitigation devices 64, a mitigation action may be appropriate where an indicating episode is not being prevented or stopped, but rather may be coped with. For example, in the case of snoring, a sound cancellation device may be used to model the snoring and send out a canceling signal so as to reduce the disruption of a sleep partner of a snoring person. Additionally, a mitigation action may be appropriate where pain is associated with the indicating episode and thus medicine may be dispensed to reduce the pain suffered by a user.

Figure 7:
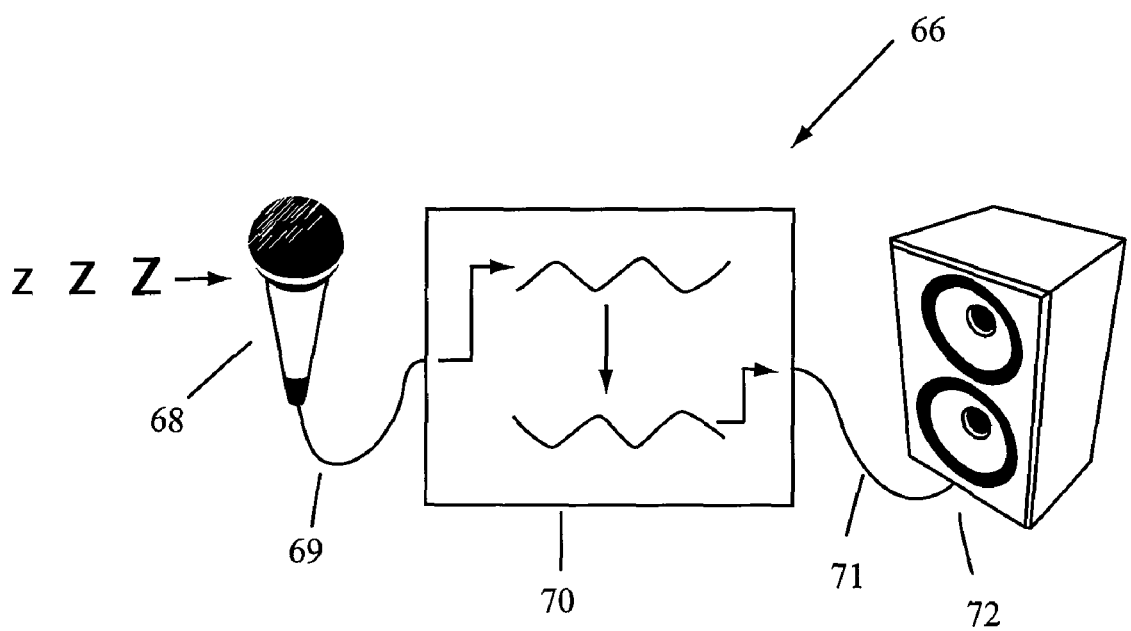
FIG. 7 is a schematic diagram of a sound cancelling mitigation device, in accordance with some examples of the present disclosure.

FIG. 7 is a schematic diagram of a sound cancelling mitigation device 66, in accordance with some examples of the present disclosure. As shown, the device 66 may include a microphone 68, which may receive a snoring sound from a snorer. An inverse waveform generator 70 may also be included with an inverting amplifier. The generator 70 may receive the sound wave from the microphone 68, via a wired or wireless connection. The inverse waveform generator 70 may create an inverse waveform and may send that wave form to a speaker 72 via a wired or wireless connection. The speaker 72 may then broadcast a sound cancelling signal making the snoring sound less apparent. As such, the effect of the snoring sound on others around the snorer may be reduced. Further discussion regarding cancellation signals may be found in patent application titled Noise Cancellation in Phone Conversation, incorporated above.

Figure 8:
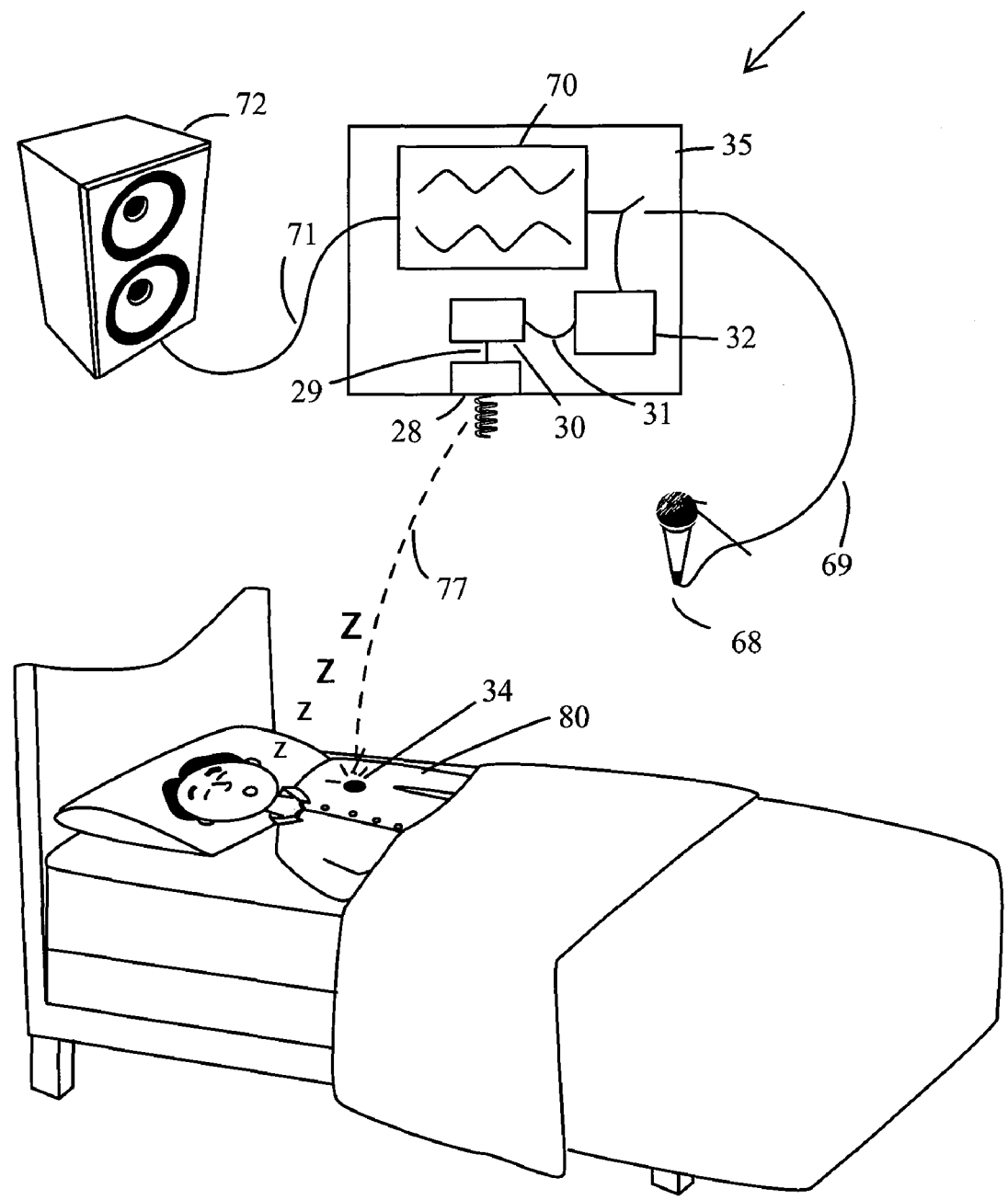
FIG. 8 is a diagram of a health-sensing device adapted to monitor a user for snoring, in accordance with some examples of the present disclosure.

Referring now to FIG. 8, the health-sensing device 34 may be adapted to monitor a user 80 for snoring in accordance with some examples of the present disclosure. In FIG. 8, the user 80 is shown with a health-sensing device 34, which may be in the form of a patch, positioned adjacent to the user's chest. In this example, the health-sensing device 34 may have a microphone-based sensor 22 for sensing sound and as such may be positioned anywhere it will reasonably pick up snoring sounds. This may be on the chest as shown, but could also be on the neck, arm, or other bodily location, or otherwise located off of the body of the user 80. When the user 80 begins to snore, snore loudly, snore continuously, or otherwise exceed a threshold, the device 34 may transmit a signal to a health-action device 35 allowing for at least a stimulation action or a mitigation action. In the case of a stimulation action, the user 80 may be stimulated with, for example, a vibratory or sound type alarm to stop the snoring. This could be any of the stimulation actions or devices discussed with respect to FIG. 6 or any other stimulation. In the case of mitigation action, the device 34 may transmit a signal allowing a sound cancellation device 66 to be activated so as to reduce the effect on the user's sleep partner. As shown, the health-sensing device 34 described in FIG. 2 may sense snoring and transmit a transmission signal 77 via a transmitter 26 to a receiver 28 of a health-action device 35 as discussed with respect to FIG. 1. The health-action device 35 may incorporate a sound cancellation device 66. The health-action device 35 may include a receiver 28, a processor 30 and a responder 32. The receiver 28 may be coupled to the processor 30, for example, with an information bus 29 for carrying information from the receiver 28 to the processor 30 in the form of a receiver signal. The processor 30 may be coupled to the responder 32, for example, with an information bus 31 for carrying information from the processor 30 to the responder 32 in the form of a responder signal.

In the present example, the health-sensing device 34 may transmit a signal indicative of a snoring event to the health-action device 35. The receiver 28 of the health-action device 35, may then send a signal to the processor 30, which may, in turn, drive the responder 32. In the present example, the responder 32 may take the form of a switch control for activating and deactivating the sound cancellation device 66. When activated, the sound cancellation device 66, as described regarding FIG. 7, may receive snoring sounds, create an inverse wave form, and emit a cancelling sound to mitigate the snoring. Alternatively, the sound canceling device 66 and the health-action device 35 could be separate units. Moreover, the microphone 68 may be omitted and the health-sensing device 34 may be adapted, not only to sense snoring and compare the snoring to a threshold as discussed, but may also be configured to record and transmit the snoring wave form to the health-action device along with the signal that indicates an indicative snoring condition. Moreover, the health-sensing device 34 and health-action device 35 may be combined into a single unit capable of sensing snoring, comparing the sound to a threshold, and selectively emitting a canceling sound.

Figure 9:
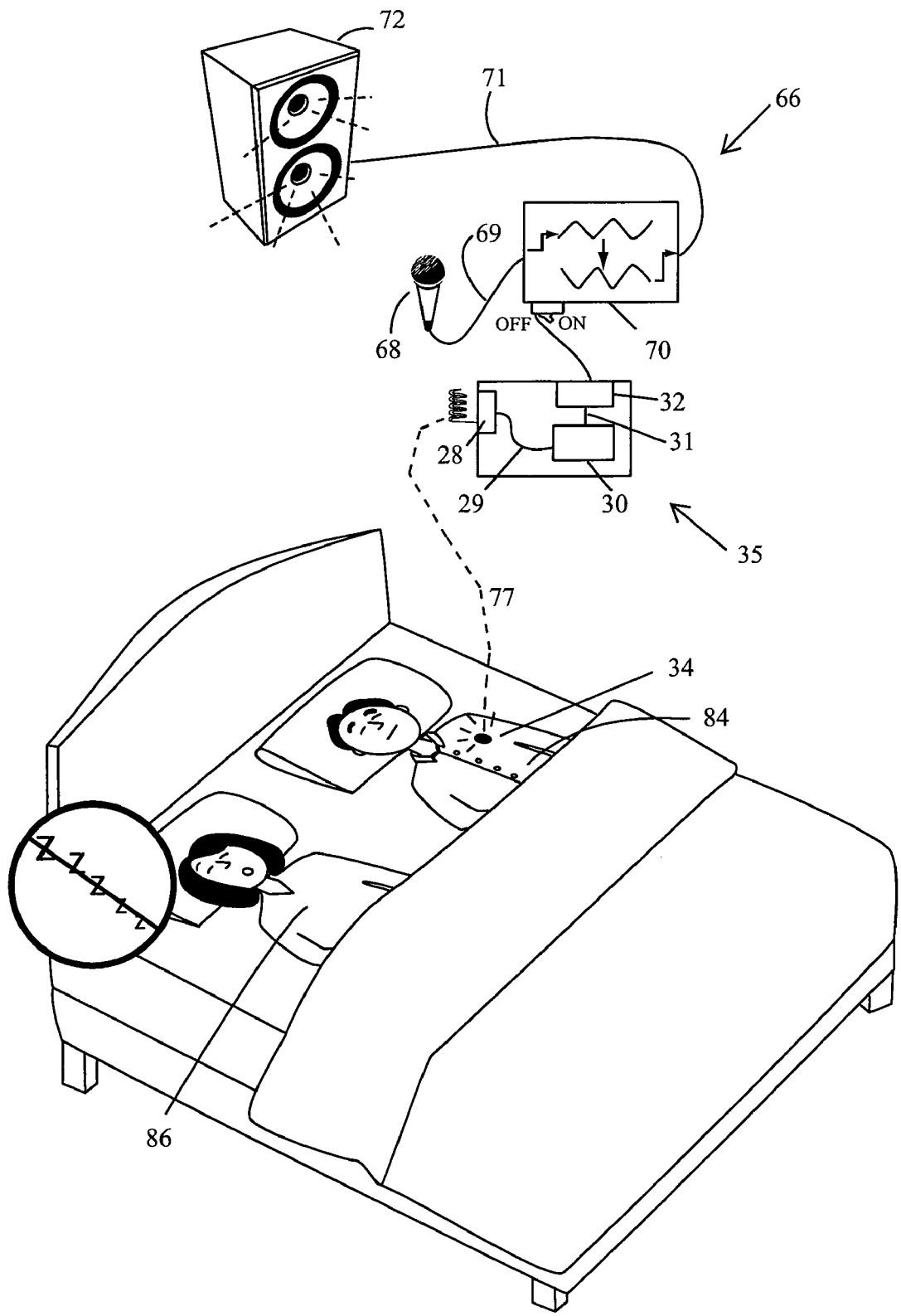
FIG. 9 is a diagram of a health-sensing device adapted to monitor a sleep partner of a snoring individual, in accordance with some examples of the present disclosure.

Referring to FIG. 9, a health-sensing device 34 may be adapted to monitor a sleep partner 84 of a snoring individual 86 in accordance with some examples of the present disclosure. That is, the sleep partner 84 may act restless or produce other measurable factors during sleep that may be detected. These measurable factors may include rapid eye movement, increased body temperature, or other movements reflecting restlessness. These acts may be detected by the sensors 22 positioned on the sleep partner 84 including a rapid eye movement sensor, a thermometer, or accelerometers consistent with the present disclosure. Other suitable sensors 22, which will detect irritation of a sleeping individual, may also be within the scope of the present disclosure. When the sleep partner becomes sufficiently agitated, the device 34 may transmit a signal to a health action device 35, which may activate a sound cancellation device 66. The cancellation device 66 may model the snoring sound and emit a cancellation signal to reduce the effect on the sleep partner 84. Alternatively, the signal may be used to activate a stimulation device to arouse the snorer sufficiently to get them to stop snoring as discussed with respect to the stimulation action of FIG. 6. As shown, the health-sensing device 34 described in FIG. 2 may sense snoring and transmit a transmission signal 77 to a health-action device 35. The health-action device 35 may include a receiver 28, a processor 30 and a responder 32. As with the health-sensing device 34, the receiver 28 may be coupled to the processor 30, for example, with an information bus 29 for carrying information from the receiver 28 to the processor 30 in the form of a receiver signal. The processor 30 may be coupled to the responder 32, for example, with an information bus 31 for carrying information from the processor 30 to the responder 32 in the form of a responder signal. In the present example, the health-sensing device 34 may transmit a signal indicative of a snoring event to the health-action device 35. The receiver 28 of the health-action device 35, may then send a signal to the processor 30, which may, in turn, drive the responder 32. In the present example, the responder 32 may take the form of a switch control for activating and deactivating the sound cancellation device 66. When activated, the sound cancellation device 66, as described regarding FIG. 7, may receive snoring sounds, create an inverse wave form, and emit a cancelling sound to mitigate the snoring. Alternatively, the sound canceling device and the health-action device 35 may be a single unit.

Other applications of similar health-sensing devices 34 and health-action devices 35 may include, but are not limited to, monitoring SIDS, elderly falls, heartbeat, and snoring as discussed in the following patent applications (incorporated above):

Sudden Infant Death Syndrome Prevention Clothing;
Elderly Fall Detection;
Microphone for Remote Health Sensing; and
Snoring Suppressant.

Figure 10:
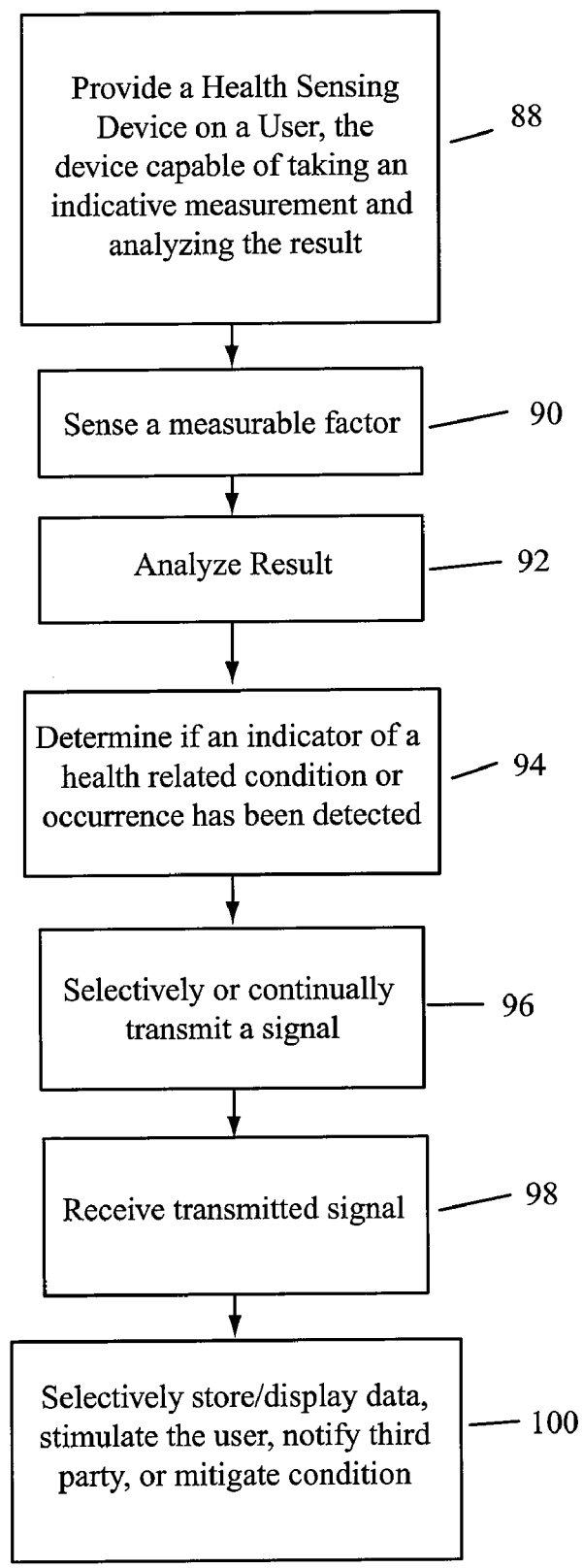
FIG. 10 is a diagram of a method of monitoring indicators of a health related condition or occurrence, in accordance with some examples of the present disclosure.

FIG. 10 is a diagram of a method of monitoring indicators of a health related condition or occurrence according to some examples of the present disclosure. The method may include one or more of operations/actions/blocks 88, 90, 92, 84, 96, 98 and 100.

The method may include providing a health-sensing device capable of taking an indicative measurement and analyzing the result at block 88. The method may further include sensing a measurable factor at block 90, analyzing the result at block 92, and determining if an indicator of a health related condition or occurrence has been detected at block 94. The method may also include selectively or continually transmitting a signal at block 96 and receiving the transmitted signal at block 98. The method may also include storing/displaying the data, stimulating the user, notifying a third party, or providing mitigation at block 100.

In some described methods, a health-sensing device 34 as discussed with respect to FIGS. 1-7 may be used. Sensing a measurable factor at block 90 may be performed by a sensor 22. In addition, analyzing the result at block 92 and determining if an indicator of a health related condition or occurrence has been detected at block 94 may be performed by a filter 24. Selectively or continually transmitting a signal and receiving the transmitted signal may each be performed by a respective transmitter 26 and receiver 28. Decisions regarding what action to take may be performed by a processor 30 and the additional step 100 may be performed by a responder 32.

Figure 11:
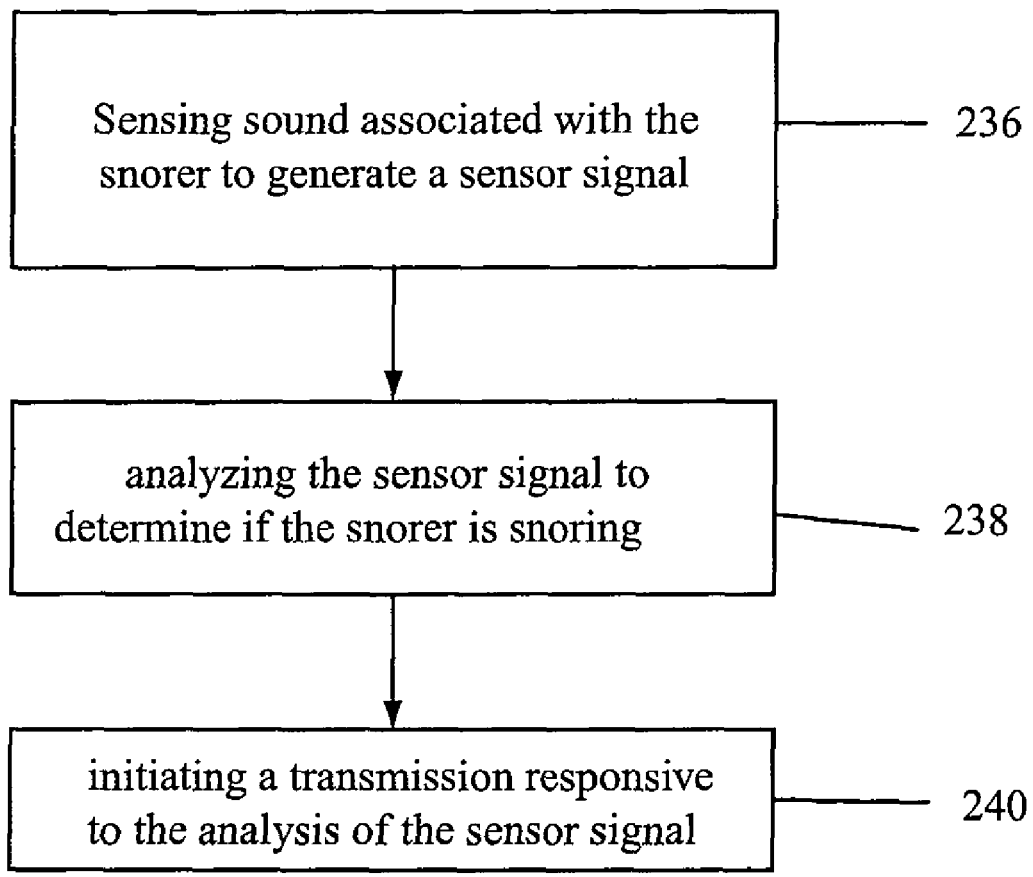
FIG. 11 is a diagram of a method of monitoring snoring, in accordance with some examples of the present disclosure.

FIG. 11 is a diagram illustrating a method for a health-sensing device to monitor a user for a health related condition is shown according to some examples of the present disclosure. The method may include one or more of operations/actions/blocks 236, 238, and 240.

The method may include sensing sound associated with the snorer to generate a sensor signal at block 236. The sensor may be provided on a substrate and the substrate may be affixed to or otherwise positioned on or adjacent the user. The method may also include analyzing the sensor signal to determine if the snorer is snoring at block 238. The method may further include initiating a transmission responsive to the analysis of the sensor signal at block 240.

In the present method, a health-sensing device 34 as discussed with respect to FIGS. 1-9 may be used. Sensing sound associated with the snorer to generate a sensor signal at block 236 may be performed by a sensor 22 in the form of, for example, a microphone. Analyzing the sensor signal to determine if the snorer is snoring at block 238 may be performed by a filter 24. Initiating a transmission responsive to the analysis of the sensor signal at block 240 may be performed by a transmitter 26.

Figure 12:
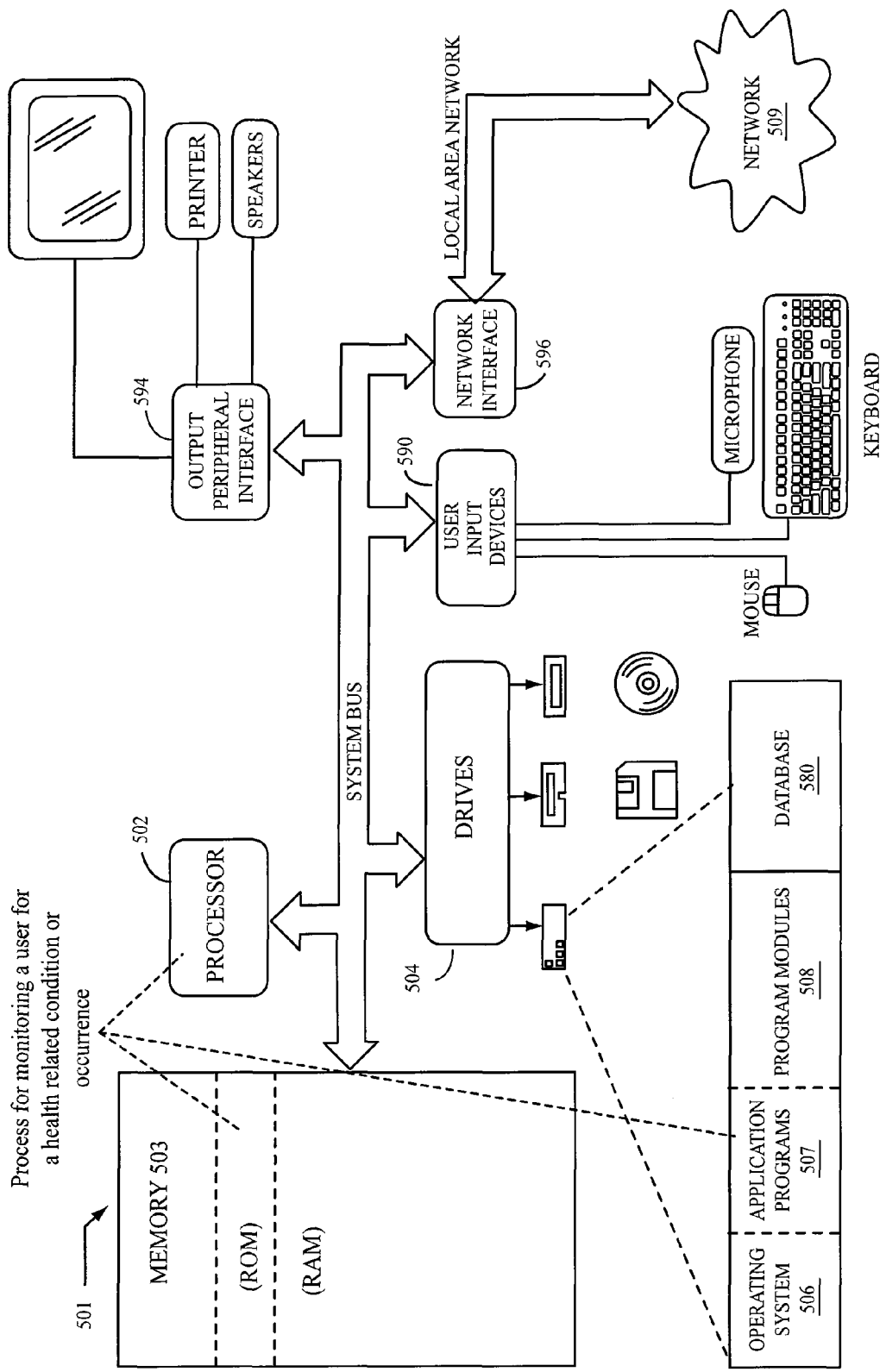
FIG. 12 is a diagram of a computing system arranged in accordance with some examples of the present disclosure.

Some or all of the elements of the health-sensing device or health-action device may be provided in a computer environment. For example, the filter of the health-sensing device or the processor of the health-action device may be provided in a computer environment. In some other examples, the health-sensing device and/or the health-action device may be provided in a computer environment. As shown in FIG. 12, a computing system may include a computer 501, including a central processing unit (CPU) or a processor, 502, main memory 503 and one or more bulk storage devices 504. The processor 502 may generally be of any desired configuration including but not limited to a microprocessor ($\mu$P), a microcontroller ($\mu$C), a digital signal processor (DSP), ASIC, or any combination thereof. Thus, the processor 502 may include logic for executing program instructions and other functional blocks such as, for example, an arithmetic logic unit (ALU), a floating point unit (FPU), a digital signal processing (DSP) core, registers, accumulators and so on. The main memory 503, which may be any suitable form of memory including, but not limited to, volatile memory such as random access memory (RAM), non-volatile memory such as read only memory (ROM) or flash memories, data storage devices such as magnetic disk storage (e.g., hard disk drive or HDD), tape storage, optical storage (e.g., compact disk or CD, digital versatile disk or DVD), or other machine-readable storage mediums that may be removable, non-removable, volatile or non-volatile. In an example, as shown in FIG. 12, a process for monitoring a user for a health related condition or occurrence may be stored in memory 503, such as the non-volatile memory. In another example, the process may be executed by running an application program 507. In still other examples, the process may be executed by the processor 502.

The bulk storage devices 504 and their associated computer storage media provide storage of computer readable instructions, data structures, program modules and other data for the computer 501. The bulk storage devices 504 may also include an operating system 506, application programs 507, program modules 508, and a database 580. The computer 501 may include user input devices 590 through which a user may enter commands and data. The user input devices may include an electronic digitizer, a microphone, a keyboard and pointing device, commonly referred to as a mouse, trackball or touch pad. Other input devices may include a joystick, game pad, satellite dish, scanner, or the like.

These and other input devices may be coupled to the processor 502 through a user input interface that may be coupled to a system bus or may be coupled by other interface and bus structures, such as a parallel port, game port or a universal serial bus (USB). Computer 501 may also include other peripheral output devices such as speakers, which may be coupled through an output peripheral interface 594 or the like.

The computer 501 may operate in a networked environment using logical connections to one or more computers, such as a remote computer coupled to network interface 596.

The remote computer may be a personal computer, a server, a router, a network PC, a peer device or other common network node, and may include many or all of the elements described above relative to computer 501. The remote computer may be considered the other of the client or the server depending on the designation of the computer 501. Networking environments are commonplace in offices, enterprise-wide area networks (WAN), local area networks (LAN), intranets and the Internet. Source and destination machines need not be coupled by a network 509 or any other means, but instead, data may be migrated via any media capable of being written by the source platform and read by the destination platform or platforms. When used in a LAN or WLAN networking environment, the computer 501 is coupled to the LAN through a network interface 596 or an adapter. When used in a WAN networking environment, computer 501 may include a modem or other means for establishing communications over the WAN, such as the Internet or network 509. Other means of establishing a communications link between the computers may be used.

Several modifications may be made to the examples disclosed herein and that the result may still be within the scope of the present disclosure. Moreover, those of skill in the art will understand and appreciate that additional uses beyond those described are within the scope of the present disclosure.

For example, the device may be adapted to monitor restless leg syndrome, seizures, or Tourette's syndrome. Restless leg syndrome may be monitored for accelerations exceeding normal accelerations experienced while sleeping. Similarly, Tourette's syndrome users and those users suffering from seizures may be monitored for accelerations exceeding those normally experienced in every day life. Several other health related conditions are directly or indirectly related to motion and application of a health-sensing device to these conditions may be within the scope of the present disclosure.

In some examples, based at least in part on the organization and proximity of the devices disclosed herein, the transmission step may not be necessary. As such, the filter and the processor may be combined in to a single filter/processor.

The foregoing describes various examples of health sensing. Following are specific examples of methods, devices, and systems of health sensing. These are for illustration only and are not intended to be limiting. In one example, a health-sensing device for a snorer may include a microphone configured to sense sound from the snorer and generate a sensor signal in response to the sensed sound, a filter configured to receive the sensor signal, determine if a snoring sound has been detected, and generate a filter signal when the snoring sound is detected, and a transmitter configured to receive the filter signal and generate a transmission responsive to the filter signal. In another example, to determine if a snoring sound has been detected, the filter is further configured to compare the sound sensed by the microphone to a threshold decibel level. In another example, the device may also include a stimulation device, wherein the filter is configured to initiate a signal driving the transmitter when snoring has been detected, the transmitter configured to send a signal to activate the stimulation device. In another example, a health-sensing system may include the above device and another device in data communication with the above device, the another device including a receiver, a processor, and a responder, wherein the processor is configured to the responder. In another example, the responder may be a sound canceling device, the sound canceling device including a microphone, a wave form generator, and a speaker, wherein the sound canceling device is configured to receive the sound, model the sound, create an inversely related sound, and emit the inversely related sound. In another example, the another device may include a sensor configured to sense sleep irritation of a sleep partner of the user and transmit a sensor signal to the filter. In another example, the filter is further configured to determine if the sleep partner is irritated and also configured to include sleep partner irritation in a decision of whether to generate the filter signal.

In another example, a health-sensing device for a sleep partner of a snorer may include a sensor configured to monitor sleep irritation of the sleep partner and generate a sensor signal in response to the monitored sleep irritation, a filter configured to receive the sensor signal, determine if the sleep partner is irritated, and generate a filter signal when irritation is detected, and a transmitter configured to receive the filter signal and generate a transmission responsive to the filter signal. In another example, the sensor is a motion based sensor adapted to sense motion of the sleep partner. In another example, the sensor is a rapid eye movement sensor adapted to sense the sleep state of the sleep partner. In another example, a health-sensing system may include the above device and another device in data communication with the above device, the another device configured to receive the transmission and generate a receiver signal and a processor configured to receive the receiver signal and generate a processor signal to drive a responder adapted to stimulate a snorer or mitigate a snoring condition. In another example, the responder is a sound canceling device adapted to mitigate a snoring condition. In another example, the sound canceling device may include a microphone adapted to receive snoring sounds, a wave form generator with an inverse wave form amplifier adapted to receive a snoring wave form from the microphone and generate an inverse wave form, and a speaker configured to emit the inverse wave form. In another example, the responder is a stimulation device adapted to stimulate the snorer. In another example, the stimulation device is further adapted to arouse the snorer.

In another example, a method for a health-sensing device to monitor a snorer may include sensing sound associated with the snorer to generate a sensor signal, analyzing the sensor signal to determine if the snorer is snoring, and initiating a transmission responsive to the analysis of the sensor signal. In another example, determining if the snorer is snoring includes comparing the sound associated with the snorer to a threshold level. In another example, the method may also include receiving the transmission and performing a process responsive to the transmission. In another example, performing a process includes stimulating the snorer with a stimulating device so as to arouse the snorer thereby interrupting the snoring. In another example, performing a process includes driving a sound canceling device. In another example, the method may also include sensing the sleep irritation of a sleep partner and determining if the sleep partner is irritated.

The present disclosure is not to be limited in terms of the particular examples described in this application, which are intended as illustrations of various aspects. Many modifications and variations may be made without departing from its spirit and scope, as may be apparent to those skilled in the art. Functionally equivalent methods and apparatuses within the scope of the disclosure, in addition to those enumerated herein, may be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which may, of course, vary. It is also to be understood that the terminology used herein is for the purpose of describing particular examples only, and is not intended to be limiting.

With respect to the use of substantially any plural and/or singular terms herein, those having skill in the art may translate from the plural to the singular or from the singular to the plural as is appropriate to the context and/or application. The various singular/plural permutations may be expressly set forth herein for sake of clarity.

It will be understood by those skilled in the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to examples containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

As will be understood by one skilled in the art, for any and all purposes, such as in terms of providing a written description, all ranges disclosed herein also encompass any and all possible subranges and combinations of subranges thereof. Any listed range may be easily recognized as sufficiently describing and enabling the same range being broken down into at least equal halves, thirds, quarters, fifths, tenths, etc. As a non-limiting example, each range discussed herein may be readily broken down into a lower third, middle third and upper third, etc. As will also be understood by one skilled in the art all language such as "up to," "at least," "greater than," "less than," and the like include the number recited and refer to ranges which may be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Claimed subject matter is not limited in scope to the particular implementations described herein. For example, some implementations may be in hardware, such as employed to operate on a device or combination of devices, for example, whereas other implementations may be in software and/or firmware. Likewise, although claimed subject matter is not limited in scope in this respect, some implementations may include one or more articles, such as a storage medium or storage media. This storage media, such as CD-ROMs, computer disks, flash memory, or the like, for example, may have instructions stored thereon, that, when executed by a system, such as a computer system, computing platform, or other system, for example, may result in execution of a processor in accordance with claimed subject matter, such as one of the implementations previously described, for example. As one possibility, a computing platform may include one or more processing units or processors, one or more input/output devices, such as a display, a keyboard and/or a mouse, and one or more memories, such as static random access memory, dynamic random access memory, flash memory, and/or a hard drive.

In the preceding description, various aspects of claimed subject matter have been described. For purposes of explanation, specific numbers, systems and/or configurations were set forth to provide a thorough understanding of claimed subject matter. However, it should be apparent to one skilled in the art and having the benefit of this disclosure that claimed subject matter may be practiced without the specific details. In other instances, well-known features were omitted and/or simplified so as not to obscure claimed subject matter. While certain features have been illustrated and/or described herein, many modifications, substitutions, changes and/or equivalents will now, or in the future, occur to those skilled in the art. It is, therefore, to be understood that the appended claims are intended to cover all such modifications and/or changes as fall within the true spirit of claimed subject matter.

The herein described subject matter sometimes illustrates different components contained within, or coupled with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Likewise, any two components so associated may also be viewed as being "operably connected", or "operably coupled", to each other to achieve the desired functionality, and any two components capable of being so associated may also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While various aspects and examples have been disclosed herein, other aspects and examples will be apparent to those skilled in the art. The various aspects and examples disclosed herein are for purposes of illustration and are not intended to be limiting, with the true scope and spirit being indicated by the following claims.

What is claimed is:

1. A health-sensing device for a snorer, the health sensing device comprising:
   a microphone sensor configured to sense sound from the snorer and generate a sensor signal in response to the sensed sound;
   a filter configured to receive the sensor signal, determine if a snoring sound has been detected, and generate a filter signal when the snoring sound is detected; and
   a transmitter configured to receive the filter signal and generate a transmission responsive to the filter signal.

2. The device of claim 1, wherein, to determine if a snoring sound has been detected, the filter is further configured to compare the sound sensed by the microphone to a threshold level.

3. The device of claim 2, further comprising a stimulation device, wherein the filter is configured to initiate a signal driving the transmitter when snoring has been detected, the transmitter configured to activate the stimulation device.

4. A health-sensing system, comprising the device of claim 1 and another device in data communication with the device of claim 1, the another device comprising a receiver, a processor, and a responder, wherein the processor is configured to drive the responder.

5. The system of claim 4, wherein the responder is a sound canceling device, the sound canceling device comprising:
   a microphone;
   a wave form generator; and
   a speaker;
   wherein the sound-canceling device is configured to receive the sound, model the sound, create an inversely related sound, and emit the inversely related sound.

6. A health-sensing system, comprising the device of claim 1 and another device in data communication with the device of claim 1, the another device comprising a sensor configured to sense sleep irritation of a sleep partner of the user and transmit a sensor signal to the filter.

7. The system of claim 6, wherein the filter is further configured to determine if the sleep partner is irritated and also configured to include sleep partner irritation in a decision of whether to generate the filter signal.

8. The device of claim 1, wherein the filter is configured to generate the filter signal responsive to a determination that the snoring sound has been detected.

9. The device of claim 1, wherein the microphone sensor, the filter, and the transmitter are configured to be worn by the snorer.

10. The device of claim 9, wherein the health-sensing device comprises a patch.

11. A health-sensing device for a sleep partner of a snorer, the device comprising:
    a sensor configured to monitor sleep irritation of the sleep partner and generate a sensor signal in response to the monitored sleep irritation;
    a filter configured to receive the sensor signal, determine if the sleep partner is irritated, and generate a filter signal when irritation is detected; and
    a transmitter configured to receive the filter signal and generate a transmission responsive to the filter signal.

12. The device of claim 11, wherein the sensor is a motion based sensor adapted to sense motion of the sleep partner.

13. The device of claim 11, wherein the sensor is a rapid eye movement sensor adapted to sense the sleep state of the sleep partner.

14. A health-sensing system, comprising the device of claim 8 and another device in data communication with the device of claim 11, the another device comprising:
    a receiver configured to receive the transmission and generate a receiver signal; and
    a processor configured to receive the receiver signal and generate a processor signal to drive a responder adapted to stimulate the snorer or mitigate the snoring condition.

15. The system of claim 14, wherein the responder is a sound canceling device adapted to mitigate the snoring condition.

16. The system of claim 15, wherein the sound canceling device comprises:
    a microphone adapted to receive snoring sounds;
    a wave form generator adapted to receive a snoring wave form from the microphone and generate an inverse wave form; and
    a speaker configured to emit the inverse wave form.

17. The system of claim 14, wherein the responder is a stimulation device adapted to stimulate the snorer.

18. The system of claim 17, wherein the stimulation device is further adapted to arouse the snorer.

19. The device of claim 11, wherein the sensor, the filter, and the transmitter are configured to be worn by the sleep partner.

20. The device of claim 19, wherein the health-sensing device comprises a patch.

21. A method for a health-sensing device to monitor a snorer, the method comprising:
    sensing sound associated with the snorer to generate a sensor signal;
    analyzing the sensor signal to determine if the snorer is snoring; and
    initiating a transmission responsive to the analysis of the sensor signal.

22. The method of claim 21, wherein determining if the snorer is snoring includes comparing the sound associated with the snorer to a threshold level.

23. The method of claim 22, further comprising receiving the transmission and performing a process responsive to the transmission.

24. The method of claim 23, wherein performing a process includes stimulating the snorer with a stimulating device so as to arouse the snorer thereby interrupting the snoring.

25. The method of claim 23, wherein performing a process includes driving a sound canceling device.

26. The method of claim 23, further comprising sensing the sleep irritation of a sleep partner and determining if the sleep partner is irritated.

27. The method of claim 21, wherein the initiating a transmission responsive to the analysis of the sensor signal comprises initiating the transmission responsive to the analysis of the sensor signal indicating a presence of snoring.

28. The method of claim 21, wherein the initiating a transmission responsive to the analysis of the sensor signal comprises initiating a transmission from a health-sensing device worn by a user to a health-action device, separate from the health-sensing device.

* * * * *

UNITED STATES PATENT AND TRADEMARK OFFICE
CERTIFICATE OF CORRECTION

PATENT NO. : 8,193,941 B2  
APPLICATION NO. : 12/436550  
DATED : June 5, 2012  
INVENTOR(S) : Wolfe et al.

Page 1 of 1

It is certified that error appears in the above-identified patent and that said Letters Patent is hereby corrected as shown below:

In Column 16, Line 22, delete "processor, 502," and insert -- processor 502, --, therefor.

In Column 22, Line 9, in Claim 14, delete "claim 8" and insert -- claim 11 --, therefor.

Signed and Sealed this  
Ninth Day of April, 2013

Teresa Stanek Rea  
*Acting Director of the United States Patent and Trademark Office*